United States Patent [19]

Pohlke et al.

[11] 3,993,759

[45] Nov. 23, 1976

[54] ANTHELMINTIC

[75] Inventors: Rolf Pohlke; Friedrich Loebich, both of Darmstadt; Herbert Thomas, Wuppertal-Elberfeld; Jurgen Thyssen, Wuppertal-Cronenberg, all of Germany

[73] Assignee: Merck Patent Gesellschaft mit beschrankter Haftung, Darmstadt, Germany

[22] Filed: Mar. 11, 1974

[21] Appl. No.: 449,690

[30] Foreign Application Priority Data
Mar. 12, 1973 Germany............................ 2312134

[52] U.S. Cl. ............................................... 424/250

[51] Int. Cl.$^2$...................................... A61K 31/495
[58] Field of Search................................... 424/250

[56] References Cited
FOREIGN PATENTS OR APPLICATIONS
1,470,062   5/1969   Germany ........................... 424/250

Primary Examiner—Jerome D. Goldberg
Attorney, Agent, or Firm—Millen, Raptes & White

[57] ABSTRACT

2-Benzoyl-4-oxo-1,2,3,6,7,11b-hexahydro-4H-pyrazino[2,1-a]isoquinoline is used as an anthelmintic against cestodes and trematodes, preferably in admixture with a pharmaceutically acceptable carrier.

20 Claims, No Drawings

ANTHELMINTIC

BACKGROUND OF THE INVENTION

This invention relates to novel anthelmintic compositions comprising a member of the class of 1,2,3,6,7,11b-hexahydro-4H-pyrazino[2,1-a]isoquinolines and having a wide spectrum of effectiveness against cestodes and trematodes.

In the literature and in practice, several compounds are known which are effective against one or more tapeworm (cestode) types, for example, niclosamide [N-(2-chloro-4-nitrophenyl)-5-chlorosalicylamide], quinacrine [2-methoxy-6-chloro-9-[(1-methyl-4-diethylaminobutyl)-amino]-acridine], dichlorophene (2,2'-dihydroxy-5,5'-dichlorodiphenylmethane), etc.

These agents, however, are in part ineffective against the larval forms of the cestodes, as well as against those adult tapeworms which are not located in the intestinal lumen. Also, the echinococci (e.g. Echinococcus granulosus) have been difficult to combat heretofore and the results have not always been certain. Additionally, with several of these agents, e.g., quinacrine and dichlorophene, considerable undesired side effects (e.g. vomiting, nausea) can be expected.

It is possible to utilize other compounds for the combating of schistosomes, for example antimony-containing agents, e.g., stibophen [sodium antimony bis(-pyrocatechol-2,4-disulfonate)], niridazole [1-(5-nitro-2-thiazolyl)-imidazolidin-2-one], lucanthone [1-(2-diethylaminoethylamino)-4-methylthiaxanthone hydrochloride], etc. However, optimum medicinal agents which are effective against the various forms of schistosomiasis, which can be utilized without problems also in mass treatments, have not been available on the market heretofore. Furthermore, no agents are as yet commercially available which are equally effective with respect to the most important types of cestodes and simultaneously with respect to schistosomes.

SUMMARY OF THE INVENTION

This invention relates to anthelmintic compositions comprising an anthelmintically effective unit dosage amount of 2-benzoyl-4-oxo-1,2,3,6,7,11b-hexahydro-4H-pyrazino[2,1-a] isoquinoline in admixture with a comestible or pharmaceutically acceptable carrier, viz., at least one solid, liquid, or semiliquid vehicle or additive, and optionally, at least one further anthelmintically effective agent.

In its method of use aspect, this invention relates to the use of the above-named compound as an anthelmintic in the human and veterinary medicine.

DETAILED DISCUSSION

The term "anthelmintic" as used herein means a composition which is effective against parasitic worms, including those existing within and also outside of the gastrointestinal tract.

2-Benzoyl-4-oxo-1,2,3,6,7,11b-hexahydro-4H-pyrazino[2,1-a] isoquinoline (Compound A) exhibits excellent and unexpected properties as an anthelmintic. Thus, the effectiveness of Compound A extends to larval and adult cestodes of a great variety of genera, e.g. Taenia sp., Hymenolepis sp., Raillietina sp., Dipylidium sp., and especially also Echinococcus sp. Surprisingly, Compound A also has a good effect on trematodes, e.g., of the genus Schistosoma, the species of which cause bilharziosis (schistosomiasis), an important tropical disease.

Compound A, as an anthelmintic, has the advantage of being widely applicable and having a low toxicity.

Thus, Compound A is effective, similarly to quinacrine, on various types of cestodes, but is less toxic than quinacrine and can also be utilized to combat the Echinococcus infection in dogs, for example, Echinococcus multilocularis.

Compound A is also effective against those tapeworms which are difficult to treat therapeutically, for example Hymenolepis nana in the ileum and Hymenolepis microstoma in the bile duct.

Compound A is effective not only against adult tapeworms, but also against the various larval forms (cysticerci), e.g., against the Cysticerci, coenuri, echinococci, cysticercoids, and plerocercoids.

In contrast to niclosamide and other tapeworm medicines, Compound A also exhibits a good effectiveness against schistosomes. In this connection, Compound A has the advantage over schistosomicidal agents such as, for example stibophen, niridazole, or lucanthone, of being less toxic than these substances, so that Compound A can be considered for the treatment of a larger number of patients suffering from bilharziosis without having to employ large numbers of medical personnel (mass treatment in infested areas).

Therefore, the active agent A can be utilized as an anthelmintic in the human as well as veterinary medicine.

Primarily, cestodes and trematodes can be combated by treatment with Compound A. The compound can be used against the following cestodes, for example, in the following hosts: 1. Ruminants: Moniezia, Stilesia, Avitellina, Thysanienzia, cysticerci of Taenia sp., Coenuris cerebralis, cysticerci of Echinococci. 2. Equines: Anoplocephala. 3. Rodents: Hymenolepis (especially H. nana and H. diminuta). 4. Fowl: Davainea, Raillietina, Hymenolepis. 5. Canines and Felines: Taenia (especially T. hydatigena, T. pisiformis, T. taeniaeformis, T. ovis, T. serialis, T. cervi, T. multiceps), Dipylidium (especially D. caninum), Echinococcus (particularly E. granulosus and E. multilocularis). 6. Humans: Taenia (especially T. solium, T. saginata, T. serialis, T. multiceps), Hymenolepis (particularly H. nana and H. diminuta), Drepanidotaenia, Dipylidium, Diplopylidium, Coenurus (especially C. cerebralis), Diphyllobothrium (particularly D. latum), Echinococcus cysticerci (especially E. granulosus and E. multilocularis).

Among the trematodes important from the viewpoint of human and veterinary medicine are primarily those of the family of the Schistosomidae, particularly those of the genus Schistosoma (Sch. mansoni, Sch. haematobium, Sch. japonicum), infestations of all of which can be treated with Compound A.

Compound A is also suitable for treatment against infestations of the genera Fasciola, Dicrocoelium, Clonorchis, Opisthorchis, Paragonimus, Paramphistomum, etc.

Compound A can be employed in numerous host and/or intermediate host organisms for combating cestodes or nematodes and/or the larvae thereof. The following species are, inter alia, the main or secondary hosts of tapeworms: humans and other primates, including the various types of monkeys, as well as the most important domestic and wild animals, e.g., the various Canidae, e.g., dog, fox, wolf, jackal; Felidae, e.g., the cat, cougar, lion, tiger; Equidae, e.g., the horse, donkey, mule; Cervidae, e.g., the deer, red deer, fallow deer; chamois, antilope, elk; rodents, e.g., hares, rabbits, rats, mice; ruminants, e.g., cattle, buffalo, sheep, goat; birds, e.g., chickens, ducks; pigs, camels, elephants, giraffes, llamas, kangaroos, fish, seals, dolphins.

Among these species, of special importance as the main host are humans and the most important domestic animals, e.g., dog, cat, horse, cattle, pig, sheep, goat, rabbit, chickens, geese.

As the location where the parasites and/or their larvae can be combated, the gastrointestinal tract is particularly applicable, for example, the stomach, the small intestine, the large intestine, the appendix, the pancreas and the bile duct. However, a good effect can also be achieved on various organs (e.g., liver, kidney, lungs, heart, spleen, lymphatic glands, brain, spinal cord, testes), the abdominal cavity, the subcutaneous, intramuscular, or subserous connective tissue, musculature, peritoneum, pleura, or diaphragm, lungs, blood vessels (such as veins, portal vein, arteries).

The use of Compound A as an anthelmintic has not been known heretofore, although Compound A has been described as an intermediate product in Federal Republic of Germany DOS No. 1,470,062. This reference also discloses an advantageous synthesis of Compound A. According to this process, isoquinoline is allowed to react, for example, with benzoyl chloride and potassium cyanide, and the thus-obtained 1-cyano-2-benzoyl-isoquinoline is subsequently hydrogenated. The resultant product is reacted with chloroacetyl chloride to the 1-(N-benzoylaminomethyl)-2-chloroacetyl-1,2,3,4-tetrahydroisoquinoline and thereafter converted into Compound A by ring closure. Agents for the cyclisation are, for example, strong bases preferably butyllithium or potassium-tert.-butylate, as well as phenyl-lithium, sodium hydride, alcoholates such as Na or K-methylate, ethylate, propylate, isopropylate, n-butylate, and tert.-butylate or amindes such as lithiumdiisopropylamide or the corresponding sodium or potassium amide. Generally, the reaction is carried out in inert solvents such as benzene, hexane, tert.-butanol, tetrahydrofuran, hexamethylphosphoric acid triamide, dioxane, ether, dimethylformamide, dimethylsulfoxide, acetonitrile, optinally in the presence of nitrogen. The reaction temperatures range between about 0° and the boiling point of the solvent used. The reaction times vary between 15 minutes and 30 hours, preferably between 10 and 14 hours depending on the temperature used.

According to another method, Compound A may be prepared by benzoylation of 4-oxo-1,2,3,6,7,11b-hexahydro-4H-pyrazino[2,1-a]isoquinoline with a benzoylating agent, preferably with benzoic acid or a functional derivative thereof. Functional derivatives are, for example, benzoates, for example, the methyl, ethyl or isopropyl esters, benzoic acid anhydride or benzoic acid halides, such as the chloride, bromide or iodide. The benzoic acid derivative may be used in excess as solvent or another inert solvent may be added, such as benzene, toluene, tetrahydrofuran, dioxane, chloroform or carbon tetrachloride. For the benzoylation preferably a basic compound is added, such as NaOH, KOH, Na- or K- carbonate, pyridine, on triethylamine. The reaction is preferably conducted at room temperature and is terminated between about 10 minutes and 48 hours, preferably between 30 minutes and 5 hours.

It is furthermore possible to prepare the benzoic acid halides in situ from benzoic acid and reagents such as silicon tetrachloride, phosphorus trichloride and phosphorus tribromide, phosphorus oxychloride or phosphorus pentachloride.

The starting material used in this reaction, 4-oxo-1,2,3,6,7,11b-hexahydro-4H-pyrazino[2,1-a]isoquinoline, is available according to different methods.

For example, by reaction with glyoxylic acid and subsequent hydrogenation 1,2,3,4-tetrahydroisoquinolyl-1-methyl-amine may be converted to N-(1,2,3,4-tetrahydroisoquinolyl-1-methyl)-glycine, which may be subjected to a cyclisation by heating to about 180° C (possibly in the presence of an inert solvent).

In the Examples 30b and 30c of the DOS No. 1 470 062 there were described also chemical solutions of Compound A. However these solution were not pharmaceutically acceptable.

Compound A is resorbed and thus is also effective against parasites outside of the gastrointestinal tract, for example, species of Schistosoma in the vascular system, *Hymenolepis microstoma* in the bile duct, and *T. hydatigena* cysticerci in the liver.

The anthelmintic effect of Compound A was manifested in both in vitro and in animal tests upon oral and parenteral application in test animals highly infested with parasites. The dosages employed were well tolerated by the test animals.

In order to be utilized as an anthelmintic, Compound A can be converted in a conventional manner into the usual pharmaceutical formulations, or mixed with a comestible.

Compound A can be used either as such, or also in a combination with a wide variety of solid, liquid and semiliquid pharmaceutically acceptable vehicles. Suitable forms of administration are, in combination with various inert vehicles, tablets, dragees, effervescent tablets; tablets or dragees containing the effective agent in depot form; capsules, granules, aqueous suspensions; injection solutions, emulsions, and suspensions; elixirs, syrups, pastes, and the like. Such vehicles comprise solid diluents or fillers, a sterile aqueous medium, as well as various nontoxic organic solvents and the like.

The tablets and the like intended for oral administration can, of course, be provided with a sweetening additive and similar substances.

The formulations are produced in the usual manner, for example, by adding the effective agents to solvents and/or excipients, optionally with the use of emulsifiers and/or dispersing agents, wherein, for example, when using water as the diluent, nontoxic organic solvents can be utilized as auxiliary solvents, if desired.

Examples of suitable auxiliary substances are: water, nontoxic organic solvents, such as paraffins (e.g., petroleum fractions), vegetable oils (e.g., peanut oil, sesame oil), alcohols (e.g., ethyl alcohol, glycerin), glycols (e.g., propylene glycol, polyethylene glycol); solid carriers, such as, for example, natural rock flours (e.g., kaolins, aluminas, talc, chalk), synthetic rock flours (e.g., highly dispersed silicic acid, silicates), sugars (e.g., cane sugar, lactose, and dextrose); emulsifiers, such as nonionic and anionic emulsifiers (e.g., polyoxyethylene fatty acid esters, polyoxyethylene fatty alcohol ethers, alkyl sulfonates, and aryl sulfonates), dispersing agents (e.g., lignin, methylcellulose, amylose [starch], and polyvinylpyrrolidone), and lubricants (e.g., magnesium stearate, talc, stearic acid, and sodium lauryl sulfate). For oral administration, tablets can, of course, also contain, in addition to the aforementioned vehicles, additives such as sodium citrate, calcium carbonate, and dicalcium phosphate, together with various extra substances, such as starch, preferably potato starch, gelatin, and the like. Furthermore, lubricants such as magnesium stearate, sodium lauryl sulfate, and talc can be utilized during the tablet-making process.

In case of aqueous suspensions and/or elixirs intended for oral administrations, the effective agent can be mixed, in addition to being mixed with the aforementioned auxiliary substances, also with various flavor-ameliorating agents or coloring agents.

The pharmaceutically acceptable carrier can also be a comestible, e.g., a component of an animal feed or in admixture with fruit juice, milk, flavored carbonated water or other palatable liquid.

In case of parenteral application, a solution of the effective agent can be used together with suitable liquid vehicles adapted for parenteral administration.

The effective agent can be utilized in the usual manner. Administration is effected preferably orally, but a parenteral, especially subcutaneous, as well as dermal application is likewise possible.

In order to effectively combat the adult forms of the cestodes, it is generally advantageous to administer effective Compound A once or several times in daily amounts of about 0.1–250, preferably about 0.5–200 mg./kg. orally and/or subcutaneously. In order to obtain efficient results when combating the corresponding tapeworm larvae (cysticerci), amounts of 1–500, preferably about 2.5–250 mg./kg. of effective agent may prove to be necessary.

For the effective combating of Schistosomes, often larger quantities of Compound A may be necessary, for example 5–500, preferably about 10–250 mg./kg.

In some cases, the aforementioned quantities may have to be varied, namely in dependence on the body weight and/or the type of administration, and also on the basis of the species of parasite and its individual behavior toward the medicine, and/or the type of the drug formulation and the time and/or interval at which the administration is effected. Thus, it is sometimes sufficient to administer less than the abovementioned minimum amount and in other cases the above-indicated upper limit is sometimes exceeded.

As will be apparent, this invention contemplates both single and repeated daily effective doses, the number being dependent upon the severity of infestation and the susceptibility of the particular parasite to Compound A.

The anthelmintically effective Compound A is preferably administered in admixture with a comestible or a pharmaceutically acceptable carrier, viz., the aforementiond vehicles and/or auxiliary agents, but it is in some cases also possible to administer Compound A in the absence of such auxiliary agents, or almost no auxiliary agents, e.g., if the Compound A is contained in capsules.

Thus, an anthelmintic preparation can be obtained by synthesis of Compound A from 1-(N-benzoyl-amino-methyl)-2-chloroacetyl-1,2,3,4-tetrahydro-isoquinoline or 4-oxo-1,2,3,6,7,11b-hexahydro-4H-pyrazino[2,1-a]isoquinoline and subsequent pharmaceutical formulation. According to this invention, a process for the preparation of an anthelmintic composition is preferred wherein 1-(N-benzoyl-aminomethyl)-2-chloroacetyl-1,2,3,4-tetrahydro-isoquinoline is subjected to a cyclisation or 4-oxo-1,2,3,6,7,11b-hexahydro-4H-pyrazino[2,1-a]isoquinoline is reacted with a benzoylating agent and the thus obtained 2-benzoyl-4-oxo-1,2,3,6,7,11b-hexahydro-4H-pyrazino[2,1-a]isoquinoline is subsequently combined with at least one solid, semisolid or liquid carrier or additive into a composition suitable for administration, optionally in combination with at least one additional active ingredient.

Depending on the manner in which the drug is administered, the ratio between Compound A and the pharmaceutically acceptable carrier, i.e., vehicle or auxiliary agent, employed can vary greatly. If Compound A is, for example, in the form of a tablet or dragee, approximately 0.1 to 5,000 mg. thereof can be combined with about 1–10,000 mg. of the pharmaceutically acceptable carrier, i.e., auxiliary agent. If Compound A is formulated as a premix for a medical fodder, approximately 1–800 g. of Compound A can be admixed to about 1 kg. of vehicle or auxiliary agent. When formulated in an injection liquid, a solution of 1 liter of liquid can contain about 5–200 g. of Compound A, depending on the type of solubilizer. Similarly, about 5–500 g. of Compound A can be dissolved or suspended in 1 liter of comestible liquid, e.g., juice.

When administering large amounts of Compound A, it is practicable in some cases to distribute several smaller individual doses over the day. For example, one can administer five separate doses of respectively 200 mg. instead of a single dose of 1000 mg.

The same dosage latitude is provided for the application in human or veterinary medicine. The other remarks set forth above are analogously applicable. The dosage ranges (in mg./kg.) for combating cestodes and trematodes in larger animals, such as humans, cattle, sheep, dogs and horses, are ordinarily lower than those given in the following Tables 1, 2 and 6 for mice and rats.

Compound A can be present in the formulations also in mixtures with other conventional effective agents.

Since the effectiveness of Compound A extends primarily to cestodes and trematodes, it is advantageous in order to reach a still broader spectrum of activity to administer it in combination, for example, with an agent effective against nematodes (roundworms). Such a suitable agent is, for example, thiabendazole [2-(4-thiazolyl)benzimidazole] or piperazine.

2-Benzoyl-4-oxo-1,2,3,6,7,11b-hexahydro-4H-pyrazino-[2,1-a]isoquinoline has an asymmetrical carbon atom and can, therefore, occur as a racemate and in the form of either of its two optical antipodes (d and l). Accordingly, the term "Compound A", viz., 2-benz-oyl-4-oxo-1,2,3,6,7,11b-hexahydro-4H-pyrazino [2,1-a]isoquinoline, includes, in addition to the racemate, its two optical antipodes. The d- and l-isomers of Compound A can be produced, for example, from the racemic 4-oxo-1,2,3,6,7,11b-hexahydro-4H-pyrazino[2,1-a]isoquinoline by reaction with, e.g., D- and L-tartaric acid, D- and L-malic acid (−)-quinic acid, or D- and L-mandelic acid, by subsequent fractional crystallization of the thus-obtained salt mixture, and finally benzoylation of the optically pure bases.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

A. PHARMACOLOGICAL EXAMPLES

EXAMPLE (a)

*Hymenolepis nana*, adults, larvae / mice

*Hymenolepis microstoma*, adults / mice

*Hymenolepis diminuta* / rats

Test animals infected experimentally with *Hymenolepis nana* or *H. microstoma* or *H. diminuta* are treated 1–3 days after infection (larvae) and/or after the prepatent period of the parasites has elapsed. The amount of effective agent is administered in the form of an aqueous suspension orally and subcutaneously, respectively.

The degree of effectiveness of the preparation is determined by counting, after dissection, the worms remaining in the test animal as compared to untreated control animals and then calculating the percentage of effectiveness.

TABLE 1

| Effective Agent | Parasite | Effective Minimum Dose Reduction Rate >90% (mg./kg.) |
|---|---|---|
| Compound A | *H. nana* - adults | 100 |
| | *H. nana* - larvae | 500 |
| | *H. microstoma* | 250 |
| | *H. diminuta* | 100 |
| Quinacrine | *H. diminuta* | >1000 |
| Niclosamide | *H. nana* - adults | 500 |
| | *H. nana* - larvae | ineffective |
| | *H. microstoma* | >500 |
| Dichlorophene | *H. nana* - adults | >1000 |
| | *H. diminuta* | 500 |

EXAMPLE (b)

*Taenia taeniaeformis* — Larvae (Cysticerci) / Mice

Mice experimentally infected with *Taenia taeniaeformis* larvae are treated about 2–5 months p. inf. The amount of active agent is orally administered in the form of an aqueous suspension.

The degree of effectiveness of the preparation is determined by counting, after dissection, the number of living and killed larvae as compared to untreated control animals, and calculating the percentage of effectiveness accordingly.

TABLE 2

| Effective Agent | Effective Minimum Dose Reduction Rate >80% (mg./kg.) |
|---|---|
| Compound A | 500 |
| Quinacrine | ineffective |
| Niclosamide | ineffective |

EXAMPLE (c)

*Taenia hydatigena* / Dogs

Dogs infected with *Taenia hydatigena* experimentally or naturally are treated after the prepatent period of the parasites has elapsed.

The effective agent is administered orally as pure active compound in gelatin capsules.

The degree of effectiveness is determined by counting the eliminated worms and the worms which have remained in the test animal, after dissection, upon completion of the treatment and calculating the percentage of eliminated worms.

TABLE 3

| Effective Agent | Effective Minimum Dose Reduction Rate ~90% (mg./kg.) |
|---|---|
| Compound A | 25 |
| Niclosamide | 50 |

EXAMPLE (d)

*Dipylidium canium* / Dogs

Dogs infected naturally with *Dipylidium caninum* are treated after the prepatent period of the parasites has elapsed.

The active agent is administered orally as a pure effective substance in gelatin capsules.

The degree of effectiveness is calculated analogously to Example (c).

TABLE 4

| Effective Agent | Effective Minimum Dose Reduction Rate ~90% (mg./kg.) |
|---|---|
| Compound A | 50 |
| Niclosamide | >100 |

EXAMPLE (e)

*Echinococcus multilocularis* / Dogs

Dogs infected experimentally with *Echinococcus multilocularis* are treated between the 25th and the 29th day p. inf.

The effective agent is administered orally as pure active compound in gelatin capsules. The degree of effectiveness is calculated analogously to Example (a).

TABLE 5

| Effective Agent | Effective Minimum Dose Reduction Rate >90% (mg./kg.) |
|---|---|
| Compound A | 100 |
| Niclosamide | insufficiently effective to ineffective |

EXAMPLE (f)

*Schistosoma mansoni* / Mice

Mice infected experimentally with *Schistosoma mansoni* are treated after the prepatent period of the parasites has elapsed. The effective agent is administered orally in an aqueous solution.

The effectiveness is determined after dissection of the test animals by counting the surviving parasites and the destroyed parasites.

TABLE 6

| Effective Agent | Effective Minimum Dose (>95% Dead Parasites; mg./kg.) |
|---|---|
| Compound A | 200 |
| Lucanthone | 250 |
| Niridazole | 500 |
| Stibophen | >1000 |

FORMULATION EXAMPLES

EXAMPLE 1

Tablets to Combat Cestodes (Adults)

a. Tablets each containing 500 mg. of Compound A as the effective agent are produced by processing a powder mixture consisting of 5 kg. of substance A, 3 kg. of lactose, 1.8 kg. of corn starch, and 0.2 kg. of magnesium stearate.

b. The same mixture can be used to manufacture tablets containing 50 mg., 250 mg., and 1000 mg. of Compound A.

The tablets containing 250 mg. and 500 mg. of Compound A as the effective agent are preferably used for purposes of human medicine; all of the above-described tablets can be utilized for purposes of veterinary medicine.

EXAMPLE 2

Tablets (Preferably) for Combating Cestode Cysticerci and/or Schistosomes a. Effervescent Tablets
Each tablet contains:

| | |
|---|---|
| Compound A | 1000 mg. |
| Citric acid | 800 mg. |
| Sodium bicarbonate | 900 mg. |
| Saccharin | 5 mg. |
| Aromatic substance | as desired |
| Lubricant | as desired |
| Coloring agent | as desired |
| Sucrose | ad 4000 mg. |

There can also be prepared tablets containing 250 mg. of Compound A; the amount of citric acid, sodium bicarbonate, saccharin and sucrose are in that case 200, 225, 1.25 and about 1000 mg, respectively. Analogous tablets with 500 mg. of Compound A contain double amounts of the other ingredients.

b. Sweet Chewable Tablets
Each tablet contains:

| | |
|---|---|
| Compound A | 2000 mg. |
| Cellulose | 80 mg. |
| Sodium carboxymethylcellulose | 40 mg. |
| Coloring agent and aromatic substance | as desired |
| Sucrose | ad 4000 mg. |

Analogously, there can also be prepared sweet chewable tablets with 250, 500 or 2000 mg. of Compound A. The amounts of the other ingredients mentioned are in these cases reduce to ⅛, ¼ and ½, respectively, of the amount given above.

EXAMPLE 3

Dragees for Combating Cestodes in Human Medicine

The dragee core contains:

| | |
|---|---|
| Compound A | 250 mg. |
| Lactose | 150 mg. |
| Corn starch | 90 mg. |
| Magnesium stearate | 10 mg. |

The dragee covering is composed of the following materials: talc, sucrose, titanium dioxide, clacium carbonate, polyvinylpyrrolidone, methylcellulose, glycerin, magnesium oxide, lacquer.

The same formulation can also be utilized for dragees containing 500 mg. of A as the active substance.

EXAMPLE 4

Elixir to Combat Cestodes (Human Medicine)

The elixir is produced by preparing a suspension from:

| | | |
|---|---|---|
| Compound A | 3.5 | kg. |
| Distilled water | 2 | l. |
| Buffer | 0.1 | l. |
| Glycerin | 3 | kg. |
| Sorbitol | 3 | kg. |
| Sucrose | 53 | kg. |
| Mixture of 60% methyl p-hydroxybenzoate and 40% propyl p-hydroxybenzoate | 0.1 | kg. |
| Ethanol | 12 | l. |

The mixture is mixed, if desired, with coloring agents and aromatic substances and filled up to 100 l. with distilled water.

EXAMPLE 5

Capsules for Combating Cestodes and Schistosomes for Human and Veterinary Medicine Capsules of an appropriate size are filled with a mixture of:

| | |
|---|---|
| Compound A | 5000 mg. |
| Talc | 250 mg. |
| Magnesium stearate | 150 mg. |

Capsules containing 1000 mg. and 10,000 mg. of Compound A are produced correspondingly.

EXAMPLE 6

Injection Fluid for Purposes of Human and Veterinary Medicine

For subcutaneous administration in an oily or aqueous suspension, 15 ml. ampoules are filled with a solution of 500 mg. of Compound A in 6 ml. of water and 4 ml. of propylene glycol with the addition of a solubilizer. The ampoules are either sterilized by heating or mixed with a preservative.

Ampoules containing 100 mg. of Compound A (for small animals) and 1000 mg. of substance A (for large animals) are correspondingly produced.

EXAMPLE 7

Pellets

From the same parts by weight of Compound A and lactose, a powder mixture is produced which is process together with sodium carboxymethylcellulose in the usual manner to a uniform granulated material having an average particle size of 1.5 mm.

EXAMPLE 8

Premix for Purposes of Veterinary Medicine Suitable for Mixing with a Fodder as the Vehicle to Produce Medical Feed a. 25% Premix (Preferably for Larger Animals)

25 weight units of substance A is mixed with
75 weight units of fine bran (wheat middlings)
and/or lactose.

b. 5% Premix (Preferably for Smaller Animals)

5 parts by weight of Compound A is processed analogously to Example 8(a).

c. Use of Premix Produced According to Example 8(a) for combating Moniezia Species in the Cattle Intestine In order to obtain a suitable medical fodder, 1 kg. of the premix produced according to Example 8(a) is mixed with 9 kg. of a conventional concentrated feed. 400 g. of this medical fodder, containing 10,000 mg. of Compound A, is administered to each adult head of cattle to combat the Moniezia infestation.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of treating cestodial and trematodial infestations in animals which comprises administering to an animal infested with cestodes or trematodes an amount of 2-benzoyl-4-oxo-1,2,3,6,7,11b-hexahydro-4H-pyrazino[2,1-a]isoquinoline effective to reduce substantially the level of infestation of the infesting cestode or trematode.

2. A method according to claim 1, wherein the administration is oral.

3. A method according to claim 1, wherein the animal is infested with a cestode.

4. A method according to claim 3, wherein the cestode is a species of Diphyllobothrium.

5. A method according to claim 3, wherein the cestode is a species of Moniezia.

6. A method according to claim 3, wherein the cestode is a species of Stilesia.

7. A method according to claim 3, wherein the cestode is a species of Dipylidium.

8. A method according to claim 3, wherein the cestode is a species of Hymenolepis.

9. A method according to claim 3, wherein the cestode is a species of Taenia.

10. A method according to claim 3, wherein the cestode is a species of Echinococcus.

11. A method according to claim 3, wherein the infested animal is a human.

12. A method according to claim 3, wherein the infested animals are cattle.

13. A method according to claim 3, wherein the animal is a dog.

14. A method according to claim 1, wherein the animal is infested with a trematode of a species of Schistosoma.

15. An anthelmintic composition adapted for oral ingestion comprising an anthelmintically effective unit dosage amount of 2-benzoyl-4-oxo-1,2,3,6,7,11b-hexahydro-4H-pyrazino[2,1-a]isoquinoline in admixture with a comestible and in the form of a veterinary feed pre-mix or in admixture with a pharmaceutically acceptable carrier and in the form of a tablet, dragee, capsule or pellets.

16. A pharmaceutically acceptable composition according to claim 15 in tablet form.

17. A pharmaceutically acceptable composition according to claim 15 in dragee form.

18. A pharmaceutically acceptable composition according to claim 15 in the form of pellets.

19. A composition according to claim 15 in the form of a veterinary feed premix.

20. A pharmaceutically acceptable composition according to claim 15 incorporated in a capsule.

* * * * *